United States Patent [19]

Earnshaw et al.

[11] Patent Number: 5,089,175

[45] Date of Patent: Feb. 18, 1992

[54] HYDROXYALKANE CARBOXYLIC ACID DERIVATIVES AND THEIR PRODUCTION

[75] Inventors: Christopher G. Earnshaw, Cambridge, United Kingdom; Gerald Kirsch, Berlin, Fed. Rep. of Germany; Petra Rach, Berlin, Fed. Rep. of Germany; Ruth Thieroff-Ekerdt, Berlin, Fed. Rep. of Germany; Michael Töpert, Berlin, Fed. Rep. of Germany

[73] Assignee: Schering Aktiengesellschaft, Berlin and Bergkamen, Fed. Rep. of Germany

[21] Appl. No.: 480,497

[22] Filed: Feb. 16, 1990

[30] Foreign Application Priority Data

Feb. 17, 1989 [DE] Fed. Rep. of Germany ....... 3905325

[51] Int. Cl.$^5$ ................................. C09F 5/08
[52] U.S. Cl. .................... 260/404; 544/106; 544/358; 546/184; 548/215; 548/240; 548/300; 540/450; 540/467; 540/470; 540/484; 540/544; 540/545; 540/612
[58] Field of Search ................ 514/788; 544/106, 358; 546/184; 548/215, 240, 300; 540/480, 467, 470, 484, 544, 545, 612

[56] References Cited

U.S. PATENT DOCUMENTS 2,372,797  4/1945  Segessemann et al. ............. 260/404
2,936,325  5/1960  Remes et al. ....................... 260/674

OTHER PUBLICATIONS

Brooks et al., Chemical Abstracts, vol. 90, #17, pp. 429, 1979.
Brooks et al., Angewandte Chemie, vol. 18, #1, pp. 72-74, 1979.
Tulloch, Chemical Abstracts, vol. 104, #17, p. 625, 1986.
Czechocki et al., Chemical Abstracts, vol. 83, #14, p. 207, 1975.
Applewhite et al., J. Am. Oil Chemist, vol. 44, #7, pp. 423-424, 1967.
Chemical Abstracts, vol. 104, No. 17, 4/28/86, p. 625.
Chemical Abstracts, Eleventh Collective Index, vols. 96-105, 1982-1986, p. 59916CS.
Chemical Abstracts, vol. 83, No. 14, 10/6/75, p. 207.
Chemical Abstracts, Ninth Collective Index, vol. 76-85, 1972-1976, p. 39705CS.
Jones et al., Microbiological Oxidation of Long-Chain Aliphatic Compounds Part IV, Alkane Derivatives Having Polar Terminal Groups, J. Chem. Soc. (C), 1968, pp. 2821-2827.

Primary Examiner—Jose G. Dees
Assistant Examiner—Deborah D. Carr
Attorney, Agent, or Firm—Millen, White & Zelano

[57] ABSTRACT

Hydroxyalkane carboxylic acid derivatives of general formula I $$R_1-O-(CH_2)_n-CON{\begin{smallmatrix}R_2\\R_3\end{smallmatrix}} \quad (I)$$

in which
  n means the numbers 7 to 18,
  $R_1$ represents a hydrogen atom or an acyl group with a maximum of 16 carbon atoms, and
  optionally an alkylene group with 4 to 8 carbon atoms interrupted by an oxygen atom or a nitrogen atom, are useful for the production of pharmaceutical agents for local treatment of diseases of the skin and mucous membranes.

7 Claims, No Drawings

HYDROXYALKANE CARBOXYLIC ACID DERIVATIVES AND THEIR PRODUCTION

SUMMARY OF THE INVENTION

The invention relates to the use of hydroxyalkane carboxylic acid derivatives of general formula I

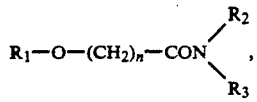

in which
n means the numbers 7 to 18,
$R_1$ represents a hydrogen atom or an acyl group with a maximum of 16 carbon atoms, and
$R_2$ and $R_3$ each mean alkyl groups with a maximum of 8 carbon atoms or together an alkylene group with 4 to 8 carbon atoms optionally interrupted by an oxygen atom or a nitrogen atom, for the production of a pharmaceutical agent for local treatment of diseases of the skin and mucous membrane.

In the publication of G. Czichocki et al. (Tensive Detergents 11, 1974, pp. 298-305) 11-hydroxyundecanoic acid diethylamide and 11-hydroxyundecanoic acid dibutylamide are previously described and 16-hydroxyhexadecanoic acid dimethylamide is mentioned in the publication of D.F. Jones et al. (J. Chem. Soc. (C), 1968, pp. 2821-2827). References to the pharmaceutical effectiveness of these substances are not found in the literature.

This invention relates particularly to previously unknown hydroxyalkane carboxylic acid derivatives of general formula Ia

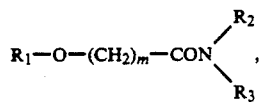

in which
$R_1$, $R_2$ and $R_3$ have the meaning mentioned in Formula I, and
m means the same meaning as n, provided that it does not mean the number 10, if $R_2$ and $R_3$ each represents an ethyl group or each represents an n-butyl group and that it does not mean the number 15, if $R_2$ and $R_3$ each represent a methyl group, their production and pharmaceutical agents (especially those for local treatment of diseases of the skin and mucous membrane), which contain these new hydroxyalkane carboxylic acid derivatives.

It is known that numerous diseases of the skin, i.a., are also caused by cornification disorders of the skin, which come about by increased formation and/or a reduced desquamation of horn cells. Thus, according to present knowledge, a cornification disorder of the follicular epithelium is involved in the origin of acne vulgaris and related diseases of the sebaceous follicle, such as, for example, acne estivalis and acne venenata besides an increased sebum production and a colonization of the follicular lumen with Propionibacterium of acne.

Ichthyosiform dermatoses and follicular hyperkeratoses are cornification disorders of the skin. Psoriasis, parapsoriasis diseases of the skin and lichenoid skin diseases are also characterized by a cornification disorder and additionally by inflammatory processes, as well as an increased blood flow and cell infiltrates.

With warts and dermatomycoses, the cornification disorder, besides the microbiological components, is important for the course of the disease.

Such diseases of the skin, linked to cornification disorders, are treated according to the known prior art with keratinolytics, such as, urea, salicylic acid or benzoyl peroxide with glucocorticoids, retinoids and, in the case of acne therapy, with antibiotics administered locally or systemically. The use of these therapeutic agents is limited either because of their limited effectiveness, as in the case of keratolytics, or because of the local toxicity as well as systemic side effects up to teratogenity of the retinoids. For this reason, the therapy possibilities for diseases, which accompany cornification disorders of the skin, so far have been unsatisfactory.

It has now been found that the hydroxyalkane carboxylic acid derivatives of general formula I surprisingly have a marked antiproliferative effect on keratinocytes, so that pharmaceutical agents, which contain these active ingredients, are very suitable for local treatment of diseases of the skin connected with cornification disorders and/or hyperproliferation of the epidermis. These hydroxyalkane carboxylic acid derivatives further show a marked comedolytic, antiinflammatory and antimicrobial effectiveness and have the advantage of a very slight toxicity, so that pharmaceutical agents containing these active ingredients can be used for local treatment of numerous diseases of the skin and mucous membrane of mammals, e.g., humans.

Specifically, such diseases are, for example:
(a) Diseases of the sebaceous glands and related diseases, such as acne vulgaris, acne venenata, special forms of endogenous acne (e.g., acne neonatorum, acne infantum, acne aestivalis, acne excoriee, and gram-negative folliculitis), rosacea, perioral dermatitis, seborrhoic dermatitis, and seborrhoic eczema.
(b) Cornification disorders of the skin, such as, for example, ichthyosiform dermatoses (e.g., ichthyosis vulgaris, sex-linked hereditary ichthyosis, lamellar ichthyosis, epidermolytic ichthyosis, and Conradi's syndrome), follicular hyper-keratoses (such as keratosis pilaris, keratosis punctata, keratosis striata, keratosis senilis, pityriasis rubra pilaris, and dyskeratosis follicularis vegetans (Darier's disease)), or localized hyperkeratoses (such as palmar and plantar hyperkeratoses and palmar and plantar keratoderm).
(c) Psoriasis and parapsoriatic diseases (such as parapsoriasis guttata, parapsoriasis variegata, and parapsoriasis en plaques).
(d) Lichenoid dermatoses (such as lichen ruber planus and lichen simplex chronicus).
(e) Warts (such as verruca vulgaris, verruca planae juvenilis, and plantar warts).
(f) Dermatomycoses (such as tinea pedis or tinea corporis).
(g) Bacterially superinfected eczemas; and
(h) Premalignant diseases of the epidermis, such as, for example, superficial actinic keratoses.

The antiproliferative effect on keratinocytes was determined in vitro as follows:

Primary cultures of neonatal murine keratinocytes are incubated in serum-free medium for 28 hours with the test substances and terminally for 4 hours with methyl-3H thymidine.

The 3H-thymidine incorporation into the DNA of the keratinocytes serves as measure for its proliferation rate. The following results were obtained in this test:

concentration are determined. Table 2 shows the results determined in this test.

TABLE 2

| Test substance | Staphylococcus aureus μg/l | | Staphylococcus epidermidis μg/l | | Streptococcus pyogenes μg/l | | Propionibacterium acnes μg/l | | Bacillus substilis μg/l | |
| --- | --- | --- | --- | --- | --- | --- | --- | --- | --- | --- |
| | MHK | MBK | MHK | MBK | MHK | MBK | MHK | MBK | MHK | MBK |
| I | >0.085 | >0.340 | >0.170 | 0.680 | 0.042 | 0.085 | 0.170 | 0.678 | 0.085 | 0.340 |
| II | 0.040 | 0.161 | 0.161 | 0.322 | 0.020 | 0.040 | 0.161 | 0.644 | 0.040 | 0.161 |
| III | >0.076 | >0.304 | >0.152 | >0.304 | 0.038 | 0.076 | >0.152 | >0.607 | >0.076 | >0.304 |
| IV | 0.098 | 0.196 | >0.196 | 0.392 | 0.025 | 0.049 | 0.196 | 0.784 | 0.049 | 0.196 |
| V | 0.053 | 0.106 | 0.214 | 0.214 | 0.013 | 0.013 | 0.106 | 0.427 | 0.053 | 0.214 |

| Test substance | Trichophyton rubrum μg/l | | Trichophyton mentagrophytes μg/l | | Microsporum canis μg/l | | Aspergillus niger μg/l | |
| --- | --- | --- | --- | --- | --- | --- | --- | --- |
| | MHK | MBK | MHK | MBK | MHK | MBK | MHK | MBK |
| I | 0.085 | 0.340 | 0.085 | 0.340 | 0.170 | 0.340 | 0.170 | 0.680 |
| II | 0.080 | 0.322 | 0.080 | 0.322 | 0.080 | 0.322 | 0.161 | 0.644 |
| III | 0.076 | 0.304 | 0.076 | 0.304 | 0.075 | 0.304 | 0.304 | 0.608 |
| IV | 0.098 | 0.392 | 0.098 | 0.392 | 0.098 | 0.392 | >0.186 | >0.784 |
| V | 0.106 | 0.427 | 0.106 | 0.427 | 0.106 | 0.427 | 0.214 | 0.427 |

I = 14-Hydroxy-tetradecanoic acid-dimethylamide
II = 13-Hydroxy-tridecanoic acid-dimethylamide
III = 12-Hydroxy-dodecanoic acid-dimethylamide
IV = 13-Hydroxy-tridecanoic acid-dipropylamide
V = 13-(2,2-Dimethylpropionyloxy)-tridecanoic acid-dimethylamide

TABLE 1

| Test Number | Substance | mol/l | % inhibition* |
| --- | --- | --- | --- |
| I | 11-hydroxyundecanoic acid dimethylamide | $10^{-5}$ $10^{-4}$ | 30% 70% |
| II | 12-hydroxydodecanoic acid dimethylamide | $10^{-5}$ $10^{-4}$ | 20% 85% |
| III | 13-hydroxytridecanoic acid dimethylamide | $10^{-5}$ $10^{-4}$ | 70% 95% |
| IV | 14-hydroxytetradecanoic acid dimethylamide | $10^{-5}$ $10^{-4}$ | 85% 90% |
| V | 13-hydroxytridecanoic acid dipropylamide | $10^{-5}$ $10^{-4}$ | 91% 92% |
| VI | 13-hydroxytridecanoic acid tetramethyleneamide | $10^{-5}$ $10^{-4}$ | 24% 92% |
| VII | 13-hydroxytridecanoic acid (2,4-dimethyl-3-oxa-pentamethylene)-amide | $10^{-5}$ $10^{-4}$ | 22% 62% |
| VIII | 13-acetoxytridencanoic acid dimethylamide | $10^{-5}$ $10^{-4}$ | 32% 89% |
| IX | 13-(2,2-dimethylpropionyloxy)-tridecanoic acid dimethylamide | $10^{-5}$ $10^{-4}$ | 86% 93% |

*relative to the vehicle control

The comedolytic effecitveness of the hydroxyalkane carboxylic acid derivatives is determined by inducing on the inside of rabbit ears by topical application of 200 microliters of tetradecane, after a 10-day treatment, comedolike changes of the hair follicles with epithelial hyperplasia and horn cell retentions and by topically applying to the sites thus treated for 11 days daily 200 microliters each of a 5% ethanolic solution of the test substance.

Then the treated areas are punched out and the shrinking of the enlarged follicular lumina is determined, which serves as a measure for the comedolytic activity In this test, a 5% solution of N,N-dimethyl-13-hydroxytridecanoic acid amide shows a 44.5% inhibition relative to the vehicle control.

To determine the antimicrobial effectiveness, suspension cultures of gram-positive bacteria and dermatophyton in the presence of serially diluted test substances are used under the usual conditions. The bacterial growth is tracked by the cloudiness of the cultures and the minimal inhibition concentration and the minimal biocidal concentration are determined. Table 2 shows the results determined in this test.

The antiinflammatory effectiveness of the hydroxyalkane carboxylic acid derivatives can be determined by the rat's ear test, which is performed as follows.

An edema is induced on the outside of rat ears by topical application of 50 microliters of 5% solution of croton oil in ethanol. At the same time, a 5% solution of the test substances in ethanol is also applied topically, 5 hours after the application the inhibition of the weight increase of the treated ear is determined, which is a measure of the antiinflammatory effectiveness of the compounds. Table 3 shows the results obtained in this test.

TABLE 3

| Number | Substance | % Inhibition* |
| --- | --- | --- |
| I | 11-hydroxyundecanoic acid dimethylamide | 54 |
| II | 12-hydroxydodecanoic acid dimethylamide | 31 |
| III | 13-hydroxytridecanoic acid dimethylamide | 64 |
| IV | 14-hydroxytetradecanoic acid dimethylamide | 55 |

*relative to the vehicle control

To determine the actue toxicity of the substances according to the invention, 100 mg/kg of 13-hydroxytridecanoic acid dimethylamide is applied interperitoneally to white mice, 6 h ours, 24 hours and 7 days after the application the general condition and the differential hemogram of the test animals had not changed noticeably.

In addition to compounds of general formula I, which carry a free hydroxy group, all compounds with an esterified hydroxy group in vivo will show the same effectiveness spectrum, since these esters will be hydrolytically cleaved in the penetration through the skin. The rate of hydrolysis of the esters and the lipophilicity of these compounds (and thus their penetration capability) will be different in different esters, by which it is possible purposefully to change the intensity of the effectiveness and the period of effectiveness of the hydroxyalkane carboxylic acid derivatives.

Suitable as acyl groups for the acyloxyalkane carboxylic acid derivatives of general formula I are those that have 1 to 16, preferably 1 to 8, carbon atoms.

Such acyl groups are, for example, straight-chain or branched alkanoyl groups, cycloalkylcarbonyl groups, cycloalkylalkanoyl groups, benzoyl groups, alkylbenzoyl groups and phenylalkanoyl groups which can be substituted in the usual way, for example, by 1 or 2 hydroxy groups, alkoxy groups (methoxy groups, etc), alkanoyloxy groups (acetoxy groups, etc.) amino groups, halogens or carboxyl groups. As suitable acyls there can be mentioned, for example: the formyl group, the acetyl group, the propionyl group, the butyryl group, the 2-methylpropionyl group, the pentanoyl group, the 2,2-dimethylpropionyl group, the hexanoyl group, the cyclopentylcarbonyl group, the 3-cyclopropylpropionyl group, the octanoyl group, the dodecanoyl group, the benzoyl group, the hydroxyacetyl group, the methoxyacetyl group, the acetoxyacetyl group, the aminoacetyl group, the 3-carboxypropionyl group, the 2-hydroxybenzoyl group, the 2-acetoxybenzoyl group, the 4-methoxyacetyl group, the 4-chlorobenzoyl group, the 4-methylbenzoyl group and the phenylacetyl group.

Because of the research conducted so far and the general principles in the art, it is evident from the fact that not only the already tested hydroxyalkane carboxylic acid derivatives and their esters have the indicated effectiveness spectrum, but that also structural analogs of these substances show a comparable effectiveness. Such structure analogs are hydroxyalkane carboxylic acid derivatives of general formula I with n meaning 7, 8 17, 18 or especially 9 and 10, 15 and 16, hydroxyalkane carboxylic acid derivatives of general formula I with $R_2$ and/or $R_3$ (which can be different) meaning an alkyl group with 2 to 8 (preferably 2 to 4) carbon atoms, such as the ethyl group, propyl group, 2-propyl group as well as hydroxyalkane carboxylic acid derivatives of general formula I with $R_2$ and $R_3$ meaning an alkylene group with 4 to 8 carbon atoms optionally interrupted with an oxygen atom or a nitrogen atom. Such alkylene groups are preferably groupings, which together with the amide nitrogen form a ring system of partial formula VI:

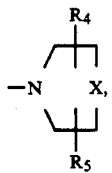
(VI)

in which
 $R_4$ and $R_5$ independent of one another represent a hydrogen atom or a methyl group and
 X symbolizes a carbon-carbon bond, a methylene group, an oxygen atom, an NH group or ->N—CH_3 group.

Such ring systems are, for example, the pyrrolidine ring, the piperidine ring, the piperazine ring and the morpholine ring as well as their derivatives carrying methyl or dimethyl substituents, e.g., on a carbon atom.

The new hydroxyalkane carboxylic acid derivatives of general formula Ia (and analogously all those of Formula I) can, for example, be produced according to a process performed under conditions which are familiar to one skilled in the art, wherein
 a) a compound of general formula II

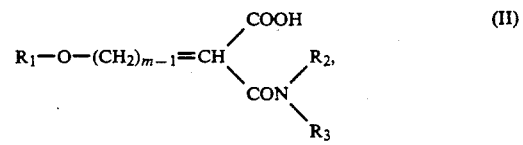

in which m is 7-18 and $R_1$, $R_2$ and $R_3$ have the meanings mentioned above, is decarboxylated, or
 b) a carboxylic acid of general formula III

in which m and $R_1$ have the above-mentioned meanings, is condensed with an amine of general formula IV

in which $R_2$ and $R_3$ have the above-mentioned meanings, or
 c) a compound of general formula V

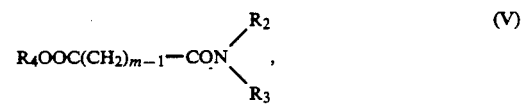

in which $R_2$ and $R_3$ have the above-mentioned meanings and $R_4$ represents an alkyl group with up to 6 carbon atoms, is reduced by catalytically activated hydrogen or complex metal hydrides and optionally the esters of general formula Ia are saponified and free alcohols of general formula Ia are esterified.

The process according to the invention according to process variant a can be is performed under conditions, which are usually used for decarboxylation of malonic acid derivatives. The reaction can take place by heating the compounds of formula I to 80° C.-180° C., and the decarboxylation can be performed in the absence of a solvent or in the presence of a high-boiling solvent (such as xylene, chlorobenzene or decaline).

The starting compounds of general formula II necessary for this process variant can be synthesized, for example, as follows:

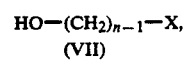
(VII)

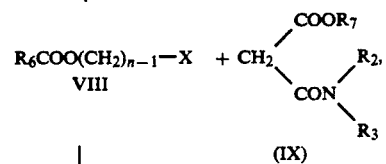 + 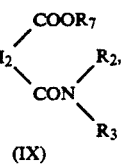
VIII                       (IX)

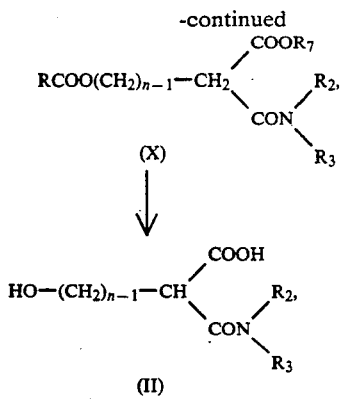

(X)

$$HO—(CH_2)_{n-1}—CH \begin{smallmatrix} COOH \\ \\ CON \end{smallmatrix} \begin{smallmatrix} R_2, \\ \\ R_3 \end{smallmatrix}$$

(II)

(In these formulas, n, $R_2$ and $R_3$ have the above-named meanings, X represents a halogen atom—e.g., chlorine, bromine or iodine —and $R_6$ as well as $R_7$ are lower alkyl groups with up to 4 carbon atoms, preferably methyl groups or ethyl groups.)

The omega-haloalkanols of formula VII used as starting compounds can be esterified, for example, with acetic hydride and then reacted with the malonic acid derivative of general formula IX under the usual conditions of malonic ester condensation (for example, by the malonic acid derivative in an aprotic solvent such as dimethylformamide being converted into the enolate by sodium hydride and the enolate being reacted with halogen compound VIII). The resulting compound of formula X can then be cleaved hydrolytically—for example with bases—and the compounds of formula II are obtained.

The process according to the invention according to process variant b can also take place under conditions known in the art. For example, it can be performed under reaction conditions, as used in the already mentioned publication of G. Czichocki et al.

The process according to the invention according to process variant c can be performed, for example, under conditions which are usually used in the reductive conversion of alkoxycarbonyl groups to hydroxymethyl groups. Thus, basically, it is possible to perform this reaction with catalytically activated hydrogen, but here there is the danger that the amide group will also be reduced at least partially. Very good results are achieved in the reduction with complex metal hydrides, especially sodium borohydride in inert solvents such as tert-butanol and methanol.

Starting compounds necessary for this process variant can be produced from the corresponding dicarboxylic acid diesters of general formula XI as follows:

$$R_8OOC(CH_2)_{n-1}—COOR_8,$$
(XI)

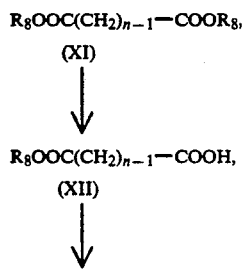

$$R_8OOC(CH_2)_{n-1}—COOH,$$
(XII)

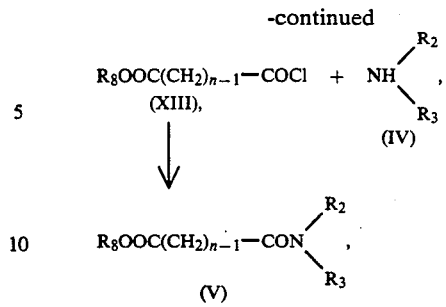

(In these formulas n, $R_2$ and $R_3$ have the above-named meanings and $R_8$ in each case represents a lower alkyl group with a maximum of 4 carbon atoms—especially the methyl group or the ethyl group.)

The dicarboxylic acid diesters of formula XI can be partially hydrolyzed with bases, for example, barium hydroxide, to the dicarboxylic acid monoesters of formula XII. These can be converted, for example, with thionyl chloride into the acid chlorides of formula XIII, which are reacted with the amines of general formula IV.

Initially it was already explained in detail that an important aspect of this invention is the use of the hydroxyalkane carboxylic acid derivatives of general formula I for the production of a pharmaceutical agent for local treatment of diseases of the skin and mucous membrane.

The production of such pharmaceutical agents to be applied topically is previously known in the art. But, on the other hand, it is also possible to make new preparations matching the special needs of the skin.

Production of such topical preparations takes place in the usual way, e.g., by the active ingredients with suitable additives being converted into the desired application form, such as a solution, a milk, a lotion, a cream, an ointment or a paste. In the preparation thus formulated, the concentration of active ingredient depends on the form of application. Preferably a concentration of active ingredient of 5 to 30% by weight is used.

The milk, lotion or cream (oil/water emulsions) and the ointment (water/oil emulsions) can be produced in the conventional way by use of conventional emulsifiers (Kirk Othmer; Encyclopedia of Chemical Technology, 3rd edition, 1979; John Wiley & Sons, New York, Vol. 8, pages 900–930, and Dr. Ott-Albrecht Neumueller: Roempps Chemie Lexikon, 7th edition, 1973; Franckhsche Verlagshandlung Stuttgart, pages 1009–1013). The waxes, emulsifiers and other additives used for these emulsions are the same as those conventionally used (Dr. Otto-Albrecht Neumueller: Roempps Chemie Lexikon, 7th edition, 1973; Franckh'sche Verlagshandlung Stuttgart, pages 1427 and 1428).

The topical preparation according to the invention can consist of one or two active ingredients, hydrophilic and/or lipophilic additives, fat phase, oil/water emulsifier, aqueous phase and preservatives.

Moisturizers (hydrocomplexes), such as, for example, propylene glycol, glycerol, polyethylene glycols, vital complexes (such as, for example, placenta extracts), enzymes, herbal extracts (such as, for example, hamamelis extract or chamomile extract) or proteins (such as, for example, collagen, can be used as hydrophilic and/or lipophilic additives. Hydrocarbons, for example squalene, petroleum jelly, paraffins or stearin, or waxes, such as, for example, beeswax or animal or vegetable oils, such as olive oil, peanut oil, fine bone oil, almond oil, jojoba oil, lanolin or sunflower oil are suitable as oily phase or fatty phase in the oil/water emulsion. Stearyl alcohol, polyoxyethylene stearate (such as, for example, MYRJ ®), complex emulsifiers (such as, for example, Amphoterin ®) and sorbitan fatty acid esters (such as, for example, Tween 80 ®), carboxyvinylpolymers (such as, for example, Carbopol ®), fatty alcohols such as, for example, cetyl alcohol, myristyl alcohol or mixed esters (such as, for example, Dehymuls ®) are suitable oil/water emulsifiers. The aqueous phase can in addition also contain buffering agents, such as, for example, disodium salt of ethylenediamine-N,N,N',N'-tetraacetic acid and preservatives such as benzoic acid, chlorquinaldol, parabene or benzalkonium chloride.

The emulsion additionally can be mixed with one or two active ingredients and optionally also with aromatic substances, such as, for example, those of the Crematest ® series and stirred until they are uniformly distributed.

It is often advantageous to add to the agents according to the invention additionally about 1 to 4% by weight of a keratolytic active substance, such as, for example, salicylic acid or resorcinol, relative to the total weight of the agent.

The agents of this invention will thus be present in a concentration routinely determined and will be applied topically analogously to related preparations such as Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosures of all applications, patents and publications, if any, cited above and below, and of corresponding application Federal Republic of Germany P 39 05 325.3, filed Feb. 17, 1989, are hereby incorporated by reference.

EXAMPLES

A) Embodiments relating to the production of hydroxyalkane carboxylic acid derivatives

EXAMPLE 1 a) 25 g of 11-bromoundecanol in 200 ml of acetic anhydride is refluxed for 5 hours. Then the excess acetic anhydride is distilled off, the residue is fractionated in a high vacuum and 28.6 g of 1-acetoxy-11-bromoundecane with a melting point of 118-120° C. at 6.7 Pa is obtained.

b) A suspension of 0.6 g of sodium hydride and 3 g of malonic acid ethyl ester dimethylamide in 30 ml of dimethylformamide is stirred for an hour at 22° C., mixed with 6.9 g of 1-acetoxy-11-bromoundecane and stirred for 16 hours at 50° C. Then the reaction mixture is stirred in 200 ml of ice water, extracted with ethyl acetate, the organic phase is dried on sodium sulfate and concentrated by evaporation in vacuum. Thus, 5.3 g of 11-acetoxyundecane malonic acid ethyl ester dimethylamide is obtained as light-yellow oil.

c) 4.04 g of the product thus obtained is suspended in 21.8 ml of 1N aqueous sodium hydroxide solution and refluxed for 5 hours. The reaction mixture is allowed to cool, is acidified with 10N aqueous hydrochloric acid, the precipitated product is suctioned off and 3.5 g of 1-hydroxyundecane malonic acid dimethylamide is obtained as crude product.

d) The resulting crude product is heated to 150° C. until the termination of the $CO_2$ cleavage (about one hour), then the mixture is allowed to cool and the resulting crude product is crystallized from ethyl acetate. Thus, 1.92 g of 13-hydroxytridecanoic acid dimethylamide with a melting point of 69-71° C. is obtained.

EXAMPLE 2 a) 200 g of tridecane-1,13-dioic acid dimethyl ester is dissolved in 200 ml of methanol, mixed with a solution of 116 g of barium hydroxide octahydrate in 1.5 of methanol and stirred for 38 hours at 22° C. Then the precipitate is suctioned off, suspended in 3 liters of ice water and acidified with 75 ml of 10 n aqueous hydrochloric acid. It is extracted with ethyl acetate, the organic phase is washed with water, dried on sodium sulfate, concentrated by evaporation in a vacuum and 179 g of tridecane-1,13-dioic acid monomethyl ester with a melting point of 50-51° C. is obtained.

b) 26.3 ml of thionyl chloride is added to 62.4 g of tridecane-1,13-dioic monomethyl ester, heated for 2 hours to 80° C. and the reaction mixture is concentrated by evaporation in a vacuum. The residue is dissolved in 50 ml of diethyl ether and is instilled within 10 minutes with ice cooling into a suspension of 67.3 ml of a 40% aqueous dimethylamine solution and 65 ml of diethyl ether. The mixture is stirred into ice water, extracted with ethyl acetate, the organic phase is washed with water, dried on sodium sulfate and concentrated by evaporation in a vacuum. The resulting crude product is recrystallized from hexane and 38.3 g of tridecane-1,13-dioic acid methyl ester dimethylamide with a melting point of 39-40° C. is obtained.

c) 10 g of tridecane-1,13-dioic acid methyl ester dimethylamide is dissolved in 140 ml of tert-butanol, mixed with 13.1 g sodium borohydride and heated to 80° C. 28 ml of methanol is instilled at 80° C. within 45 minutes. The mixture is allowed to cool, mixed with 350 ml of ice water and extracted with ethyl acetate, the organic phase is washed, dried on sodium sulfate and concentrated by evaporation in a vacuum. The resulting crude product is recrystallized from cyclohexane-ethyl acetate and 6.4 g of 13-hydroxytridecanoic acid dimethylamide with a melting point of 68-70° C. is obtained.

EXAMPLE 3

11-Hydroxyundecanoic acid dimethylamide is produced under the conditions of example 2 but starting from undecane-1,11-dioic acid dimethyl ester.

EXAMPLE 4

12-Hydroxydodecanoic acid dimethylamide is produced under the conditions of example 2 but starting from dodecane-1,12-dioic dimethyl ester.

EXAMPLE 5

14-Hydroxytetradecanoic acid dimethylamide is produced under the conditions of example 2 but starting from tetradecane-1,14-dioic acid dimethyl ester.

EXAMPLE 6

15.0 g of 13-hydroxytridecanoic acid dimethylamide is mixed with 64.7 ml of acetic anhydride and 80.4 ml of pyridine and stirred for 16 hours at room temperature. Then the mixture is poured on ice water, extracted with ethyl acetate, the organic phase is washed, dried on sodium sulfate and concentrated by evaporation in a vacuum. The formed crude product is recrystallized from hexane and 13.27 g of 13-acetoxytridecanoic acid dimethylamide with a melting point of 44–45.5° C. is obtained.

EXAMPLE 7

84.2 ml of 2,2-dimethylpropionic acid chloride is instilled in a mixture of 15.0 g of 13-hydroxytridecanoic acid dimethylamide and 80 ml of pyridine with ice cooling. The reaction mixture is stirred for 14 hours at room temperature and poured onto ice water. After addition of 70 g of sodium bicarbonate, it is extracted with ethyl acetate, the organic phase is washed, dried on sodium sulfate and concentrated by evaporation in a vacuum. The resulting crude product is chromatographed over a silica gel column (8×30 cm) with ethyl acetatehexane (1+1) and 13.6 g of 13-(2,2-dimethylpripionyloxy)-tridecanoic acid dimethylamide with a melting point of 22° C. is obtained.

EXAMPLE 8 a) 176.1 g of tridecane-1,13-dioic acid monomethyl ester is mixed with 74.2 ml of thionyl chloride and 5.6 ml dimethylformamide and stirred for 90 minutes at 80° C. Then the mixture is concentrated by evaporation in a vacuum and 191 g of crystalline tridecane-1,13-dioic acid chloride methyl ester is obtained as crude product.

b) A solution of 27.21 ml of dipropylamine in 25 ml of diethyl ether is instilled in a solution of 25.0 g of tridecane-1,13-dioic acid chloride methyl ester crude product in 100 ml of diethyl ether at −10° C. 60 ml of diethyl ether is further added to the mixture and stirred for 150 minutes more at 0° C. The reaction mixture is poured into a mixture of ice/dilute hydrochloric acid and extracted with diethyl ether. The organic phase is washed, dried on sodium sulfate, concentrated by evaporation in a vacuum and 29.34 g of 29.34 g of tridecane-1,13-dioic acid methyl ester dipropylamide is obtained as crude product.

c) 68.8 ml of methanol is instilled in a boiling suspension of 29.34 g of tridecane-1,13-dioic acid methyl ester dipropylamide in 400 ml of tert-butanol and 32.2 g of sodium borohydride under inert gas within 45 minutes. Then the reaction mixture is refluxed for 100 minutes more, allowed to cool and poured into a mixture of ice, water and sodium chloride. It is extracted with ethyl acetate, the organic phase is washed with saturated aqueous sodium chloride solution, dried on sodium sulfate and concentrated by evaporation in a vacuum. The residue is chromatographed over a silica gel column (7×35 cm) with ethyl acetate/hexane (1+1) and 14.3 g of 13-hydroxytridecanoic acid dipropylamide with a melting point of 33.5–35.0° C. is obtained

EXAMPLE 9 a) 25.0 g of tridecane-1,13-dioic acid chloride methyl ester is reacted with 16.6 ml of pyrrolidine under the conditions of example 8b, workedup and 24.32 g of tridecane-1,13-dioic acid methyl ester tetramethyleneamide with a melting point of 41–42° C. is obtained.

b) 62.6 ml of methanol is instilled in a boiling suspension of 24.32 g of tridecane-1,13-dioic acid methyl ester tetramethyleneamide in 350 ml of tert-butanol and 29.28 g of sodium borohydride within 30 minutes. The mixture is refluxed for 150 more minutes and worked up as described in example 8c. The crude product thus obtained is recrystallized from cyclohexane/ethyl acetate and 13.53 g of 13-hydroxytridecanoic acid tetramethyleneamide with a melting point of 60–61° C. is obtained.

EXAMPLE 10 a) 25.0 g of tridecane-1,3-dioic acid chloride methyl ester is reacted with 15.8 ml of 2,6-dimethylmorpholine under the conditions of example 8b and worked up. The resulting crude product is chromatographed on a silica gel column (5×100 cm) with hexane-ethyl acetate/hexane (1+2) gradient and 104 g of tridecane-1,13-dioic acid methyl ester-(2,4-dimethyl-3-oxapentamethylene)amide is obtained as oil.

b) 26.27 ml of methanol is instilled in a boiling suspension of 10.2 g of tridecane-1,13-dioic acid methyl ester-(2,4-dimethyl-3-oxapentamethylene)amide in 150 ml of tert-butanol and 12.28 g of sodium borohydride within 20 minutes. Then the mixture is refluxed for 150 minutes more, worked up as in example 8c, the resulting crude product is crystallized from cyclohexane/ethyl acetate and 5.58 g of 13-hydroxytridecanoic acid-(2,4-dimethyl-3-oxapentamethylene)amide with a melting point of 86–87.5° C. is obtained.

B) Embodiment relating to a galenical preparation

| Composition | % by weight |
|---|---|
| 13-Hydroxytridecanoic acid dimethylamide | 20.0 |
| Benzoic acid | 0.1 |
| Salicylic acid | 2.0 |
| Glycerol monostearate | 2.0 |
| Cetyl alcohol | 3.0 |
| Polyoxyethylene(20)sorbitanmonooleate | 5.0 |
| Sodium lauryl ether sulfate | 10.0 |
| Ethanolamine lauryl ether sulfate | 2.0 |
| Olive oil | 2.0 |
| Ascorbic acid | 1.0 |
| Bidistilled water | 53.9 |

Preparation

13-Hydroxytridecanoic acid dimethylamide, benzoic acid, polyoxyethylene(20)sorbitanmonooleate, sodium lauryl ether sulfate, ethanolamine lauryl ether sulfate and water are warmed to 60° C. and dispersed with the mixture of salicyclic acid, glycerol monostearate, cetyl alcohol, olive oil and ascorbic acid at 40° C.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A hydroxyalkane carboxylic acid derivative of the formula Ia

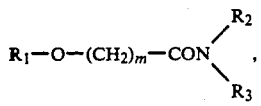 (Ia)

wherein $R_1$ is a hydrogen atom or $C_{1-16}$-acyl group, and $R_2$ and $R_3$ are each independently $C_{1-8}$-alkyl, or together are $C_{4-8}$-alkylene or $C_{4-8}$-alkylene interrupted by oxygen and/or nitrogen, and m is 11 to 14.

2. 12-Hydroxydodecanoic acid dimethylamide,

13-Hydroxytridecanoic acid dimethylamide,

14-Hydroxytetranoic acid dimethylamide,

13-Acetoxytridecanoic acid dimethylamide, 13-(2,2-Dimethylpropionyloxy)-tridecanoic acid dimethylamide, 13-Hydroxytridecanoic acid dipropylamide, 13-Hydroxytridecanoic acid tetramethyleneamide, or 13-Hydroxytridecanoic acid-(2,4-dimethyl-3-oxapentamethylene)-amide, each a compound of claim 1.

3. A carboxylic acid derivative according to claim 1, wherein $R_1$ is $C_{1-8}$-acyl.

4. A carboxylic acid derivative according to claim 1, wherein $R_1$ is alkanoyl, cycloalkylcarbonyl, cycloalkylalkanoyl, benzoyl, alkylbenzoyl or phenylalkanoyl, optionally substituted by hydroxy, alkoxy, alkanoyloxy, amino, halogen or carboxy.

5. A carboxylic acid derivative according to claim 1, wherein one of $R_2$ or $R_3$ is $C_{2-4}$-alkyl or $R_2$ and $R_3$ together with the nitrogen atom from an alkylene group of formula VI:

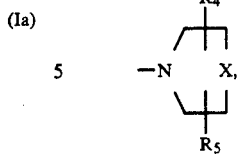 (VI)

wherein $R_4$ and $R_5$ are each independently hydrogen or methyl and X is a carbon-carbon bond, a methylene group, an oxygen atom, an NH group or an N-CH$_3$ group.

6. A carboxylic acid derivative according to claim 5, wherein $R_2$ and $R_3$ together form a pyrrolidine, piperidine, piperazine or morpholine ring, or one of said rings substituted by one or two methyl groups.

7. A process for the production of hydroxyalkane carboxylic acid derivatives of general formula Ia according to claim 1, wherein

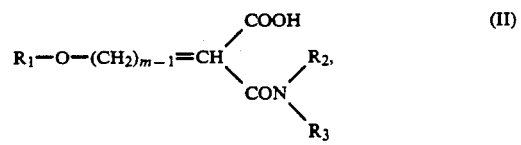 (II)

in which m, $R_1$, $R_2$ and $R_3$ have the meaning mentioned in claim 1, is decarboxylated, or a compound of general formula V

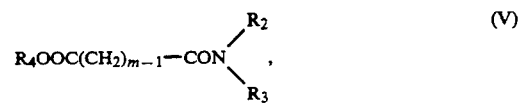 (V)

in which $R_2$ and $R_3$ have the above-mentioned meaning and $R_4$ represents an alkyl group with up to 6 carbon atoms, is reduced by catalytically activated hydrogen or complex metal hydrides and optionally the esters of general formula Ia are saponified and free alcohols of general formula Ia are esterified.

* * * * *